(12) United States Patent
Sirinyan et al.

(10) Patent No.: US 6,369,054 B1
(45) Date of Patent: Apr. 9, 2002

(54) AQUEOUS AGENTS FOR COMBATING PARASITIC INSECTS AND ACARINA IN HUMAN BEINGS

(75) Inventors: Kirkor Sirinyan, Gladbach; Karin Horn, Solingen; Ronald Helmut Stöcker, Monheim; Rainer Sonneck, Leverkusen, all of (DE)

(73) Assignee: Bayer AG, Leverkusen (DE)

( * ) Notice: Subject to any disclaimer, the term of this patent is extended or adjusted under 35 U.S.C. 154(b) by 0 days.

(21) Appl. No.: 09/601,572

(22) PCT Filed: Feb. 10, 1999

(86) PCT No.: PCT/EP99/00878

§ 371 Date: Aug. 3, 2000

§ 102(e) Date: Aug. 3, 2000

(87) PCT Pub. No.: WO99/41987

PCT Pub. Date: Aug. 26, 1999

(30) Foreign Application Priority Data

Feb. 23, 1998 (DE) ......... 198 07 630

(51) Int. Cl.$^7$ ......... A61K 31/41; A61K 31/42; A61K 31/415; A61K 31/34

(52) U.S. Cl. ......... 514/229.2

(58) Field of Search ......... 514/229.2, 241, 514/242, 245, 247, 256, 332, 333, 359, 374, 385, 396, 461

(56) References Cited

U.S. PATENT DOCUMENTS

| | | |
|---|---|---|
| 4,590,272 A | 5/1986 | Shiokawa et al. ......... 544/335 |
| 4,680,294 A | 7/1987 | Shiokawa et al. ......... 514/256 |
| 4,742,060 A | 5/1988 | Shiokawa et al. ......... 514/252 |
| 4,803,277 A | 2/1989 | Shiokawa et al. ......... 514/332 |
| 4,806,553 A | 2/1989 | Shiokawa et al. ......... 514/332 |
| 4,812,454 A | 3/1989 | Shiokawa et al. ......... 514/256 |
| 4,812,571 A | 3/1989 | Shiokawa et al. ......... 546/296 |
| 4,849,432 A | 7/1989 | Shiokawa et al. ......... 514/341 |
| 4,914,113 A | 4/1990 | Shiokawa et al. ......... 514/333 |
| 4,918,086 A | 4/1990 | Gsell ......... 514/351 |
| 4,918,088 A | 4/1990 | Gsell ......... 514/357 |
| 4,948,798 A | 8/1990 | Gsell ......... 514/275 |
| 4,963,572 A | 10/1990 | Gsell ......... 514/357 |
| 4,963,574 A | 10/1990 | Bachmann et al. ......... 514/357 |
| 5,034,524 A | 7/1991 | Shiokawa et al. ......... 544/134 |
| 5,039,686 A | 8/1991 | Davies et al. ......... 514/341 |
| 5,304,566 A | 4/1994 | Ishimitsu et al. ......... 514/357 |
| 5,489,603 A | 2/1996 | Uneme et al. ......... 514/365 |
| 5,637,295 A | 6/1997 | Lang et al. ......... 424/70.2 |
| 5,750,548 A | 5/1998 | Friedel et al. ......... 514/357 |
| 6,001,858 A | * 12/1999 | Sirinyan et al. ......... 514/341 |

FOREIGN PATENT DOCUMENTS

| | | | |
|---|---|---|---|
| AU | 604109 | 10/1988 | ......... C07D/417/06 |
| DE | 4443888 | 6/1996 | ......... A01N/43/50 |
| DE | 19540948 | 5/1997 | ......... A01N/43/50 |
| DE | 19543477 | 5/1997 | ......... A01N/43/653 |
| DE | 19613334 | 10/1997 | ......... A01N/43/50 |
| EP | 0135956 | 4/1985 | ......... C07D/279/06 |
| EP | 0189972 | 8/1986 | ......... C07D/279/06 |
| EP | 0302389 | 2/1989 | ......... C07D/213/36 |
| EP | 0306696 | 3/1989 | ......... C07D/401/06 |
| EP | 0364844 | 4/1990 | ......... C07D/213/61 |
| EP | 0375907 | 7/1990 | ......... C07D/213/61 |
| EP | 0383091 | 8/1990 | ......... C07D/213/61 |
| EP | 0386565 | 9/1990 | ......... C07D/413/06 |
| EP | 0425978 | 5/1991 | ......... C07D/213/61 |
| EP | 0428941 | 5/1991 | ......... C07D/251/04 |
| EP | 0455000 | 11/1991 | ......... C07D/401/06 |
| EP | 0464830 | 1/1992 | ......... C07F/9/6506 |
| EP | 0471372 | 2/1992 | ......... C07D/277/32 |
| EP | 0580533 | 10/1995 | ......... A62D/3/00 |
| GB | 2245935 | 1/1992 | ......... F04C/2/10 |
| WO | 9117659 | 11/1991 | ......... A01N/35/08 |
| WO | 9737544 | 10/1997 | ......... A01N/51/00 |

OTHER PUBLICATIONS

Ziolkowsky, B., "Neue Haarbehandlungsmittel", SOFW–Journal, 123:822–824 (1997).

Zülli, F., and Suter, F., "Preparation and properties of small nanoparticles for skin and hair care", SOFW–Journal, 123:880–885 (1997).

*Agricultural Chemistry*, p. 6, JP(A)–C, Week 9145, NITN, 91–329220/45, J0–3220–176–A, "New trio:fluoro–acetyl deriv. for insecticide–prepd. e.g. by reacting 1–(2–chlor–5–phenyl methylamino)–1–methylio–2–fluoro acetylethylene with methylamine and ethanol", Nihon Bayer Agrochem KK, Jan. 23, 1990, JP–011947.

*Agricultural Chemistry*, p. 3, JP(A)–C, Week 9039, NITN, 90–294309/39, J0–2207–083–A, "Prepn. of 2–nitro–imino–imidazolidine(s)—by alkylation reaction in presence of base and phase transfer catalyst in inactive solvent", Nihon Tokushu Noyaku Sei, Feb. 4, 1989, JP–024782.

(List continued on next page.)

Primary Examiner—Alton Pryor

(57) ABSTRACT

The present invention relates to water-containing formulations for the dermal control of parasitic insects and mites on humans, said formulations having the following composition:

a—agonists or antagonists of the nicotinic acetylcholine receptors of insects in a concentration of from 0.0001 to 7.5% by weight, based on the overall weight of the formulation;

b—water in a concentration of from 20 to 50% by weight, based on the overall weight of the formulation;

c—acyclic alcohols in a concentration of from 20 to 50% by weight, based on the overall weight of the formulation;

d—solvents from the group consisting of cyclic carbonates and lactones in a concentration of from 2.5 up to 20.0% by weight, based on the overall weight of the formulation;

e—optionally further auxiliaries from the group consisting of thickeners, spreading agents, colorants, antioxidants, propellants, preservatives, tackifiers, emulsifiers, in a concentration of from 0 up to 30% by weight, based on the overall weight of the formulation.

14 Claims, No Drawings

OTHER PUBLICATIONS

*Agricultural Chemistry* p. 2, J6–C, Week 8905, NITN, 89–035258/05, J63307–857–A, "New cyano–alkyl–heterocyclic cpds. for insecticides–are prepd. e.g. by reacting 2–cyano–imino tetra:hydro–1,3–thiazine with 3–chloropropionitrile, etc.", Nihon Tokushu Noyaku Sei, Jun. 9, 1987, JP–142150.

*Agricultural Chemistry* pp. 4–5, J6–C, Week 8902, NITN, 89–011891/02, J63287–764–A, "New N–3–Cyano:benzyl–heterocyclic cpds.—useful as insecticides", Nihon Tokushu Noyaku Sei, May 21, 1987, JP–122516.

*Agricultural Chemistry*, p. 9, JP(A)–C, Week 9204, ISHH, 92–030646/04, J0–3279–359–A, "New chloro–pyridyl:methyl nitro:guanidine derivs. useful as harmful organisms esp. insects, nematodes and acarids exterminating agent", Ishihara Sango Kaisha, Mar. 27, 1990, JP–077220.

*Agricultural Chemistry*, p. 4, JP(A)–C, Week 9201, NIPS, 92–002652/01, J0–3255–072–A, "New methylamino nitro:ethylene derivs. useful as insecticides", Nippon Soda KK, Jan. 11, 190, JP–003855.

\* cited by examiner

AQUEOUS AGENTS FOR COMBATING PARASITIC INSECTS AND ACARINA IN HUMAN BEINGS

This Appl'n is a 371 of PCT/EP99/00878 filed Feb. 10, 1999.

The present invention relates to water-containing formulations for the dermal control of parasitic insects and mites on humans by means of agonists or antagonists of the nicotinic acetylcholine receptors of insects.

Agonists or antagonists of the nicotinic acetylcholine receptors of insects are known. They include the nicotinyl insecticides and, very particularly, the chloronicotinyl insecticides.

DE-A-19 613 334 discloses formulations for dermal application of agonists or antagonists of the nicotinic acetylcholine receptors which are suitable for controlling parasitic insects and mites on humans. These formulations are based on mixtures of organic solvents.

This invention, accordingly, provides novel water-containing formulations for dermal application of agonists or antagonists of the nicotinic acetylcholine receptors which are suitable for controlling parasitic insects and mites, of the following composition:

a—agonists or antagonists of the nicotinic acetylcholine receptors of insects in a concentration of from 0.0001 to 7.5% by weight, based on the overall weight of the formulation;

b—water in a concentration of from 20 to 50% by weight, based on the overall weight of the formulation;

c—acyclic alcohols in a concentration of from 20 to 50% by weight, based on the overall weight of the formulation;

d—cyclic carbonates in a concentration of from 2.5 up to 20.0% by weight, based on the overall weight of the formulation;

e—optionally further auxiliaries from the group consisting of thickeners, spreading agents, colorants, antioxidants, propellants, preservatives, tackifiers, emulsifiers, in a concentration of from 0 up to 30% by weight, based on the overall weight of the formulation.

Agonists or antagonists of the nicotinic acetylcholine receptors of insects are known, for example, from the European Published Specifications No. 580 553, 464 830, 428 941, 425 978, 386 565, 383 091, 375 907, 364 844, 315 826, 259 738, 254 859, 235 725, 212 600, 192 060, 163 855, 154 178, 136 636, 303 570, 302 833, 306 696, 189 972, 455 000, 135 956, 471 372, 302 389; the German Published Specifications No. 3 639 877, 3 712 307; the Japanese Published Specifications No. 03 220 176, 02 207 083, 63 307 857, 63 287 764, 03 246 283, 04 9371, 03 279 359, 03 255 072; the U.S. Pat. Specifications No. 5,034,524, 4,948, 798, 4,918,086, 5,039,686, 5,034,404; the PCT Applications No. WO 91/17 659, 91/4965; the French J Application No. 2 611 114; the Brazilian Application No. 88 03 621.

The compounds described in these publications and their preparation is expressly incorporated herein by reference.

These compounds are preferably represented by the general formula (I)

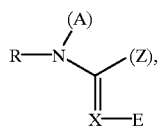

in which

R represents hydrogen, optionally substituted radicals from the group consisting of acyl, alkyl, aryl, aralkyl, heteroaryl or heteroarylalkyl;

A represents a monofunctional group from the group consisting of hydrogen, acyl, alkyl, aryl or represents a bifunctional group which is linked to the radical Z;

E represents an electron-withdrawing radical;

X represents the radicals —CH= or =N— where the radical —CH= may be linked to the radical Z instead of an H atom;

Z represents a monofunctional group from the group consisting of alkyl, —O—R, —S—R,

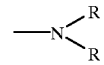

or represents a bifunctional group which is linked to the radical A or the radical X.

Particular preference is given to the compounds of the formula (I) in which the radicals are as defined below:

R represents hydrogen and also represents optionally substituted radicals from the group consisting of acyl, alkyl, aryl, aralkyl, heteroaryl, heteroarylalkyl, heterocyclylalkyl.

Acyl radicals which may be mentioned are formyl, alkylcarbonyl, arylcarbonyl, alkylsulphonyl, arylsulphonyl, (alkyl-)-(aryl-)-phosphoryl, which for their part may be substituted.

Alkyls which may be mentioned are $C_{1-10}$-alkyls, in particular $C_{1-4}$-alkyl, specifically methyl, ethyl, i-propyl, sec- or t-butyl, which for their part may be substituted.

Aryls which may be mentioned are phenyl, naphthyl, in particular phenyl.

Aralkyls which may be mentioned are phenylmethyl, phenylethyl.

Heteroaryls which may be mentioned are heteroaryl having up to 10 ring atoms and N, O or S, in particular N, as heteroatoms. Specifically, mention may be made of thienyl, furyl, thiazolyl, imidazolyl, pyridyl, benzothiazolyl.

Heteroarylalkyls which may be mentioned are heteroarylmethyl, heteroarylethyl, where the heteroaryl preferably contains up to 6 ring atoms and N, O or S, in particular N, as heteroatoms. Particular preference is given to the abovementioned heteroaryl radicals.

Heterocyclylalkyl which may be mentioned is tetrahydrofuranylmethyl.

Substituents which may be mentioned by way of example and by way of preference are:

alkyl preferably having 1 to 4, in particular 1 or 2, carbon atoms, such as methyl, ethyl, n- and i-propyl and n-, i- and t-butyl; alkoxy preferably having 1 to 4, in particular 1 or 2, carbon atoms, such as methoxy, ethoxy, n- and i-propyloxy and n-, i- and t-butyloxy; alkylthio preferably having 1 to 4, in particular 1 or 2, carbon atoms, such as methylthio, ethylthio, n- and i-propylthio and n-, i- and t-butylthio; halogenoalkyl preferably having 1 to 4, in particular 1 or 2, carbon atoms and preferably 1 to 5, in particular 1 to 3, halogen atoms, where the halogen atoms are identical or different and are preferably fluorine, chlorine or bromine, in particular fluorine, such as trifluoromethyl; hydroxyl, halogen, preferably fluorine, chlorine, bromine and iodine, in particular fluorine, chlorine and bromine; cyano; nitro; amino; monoalkyl- and dialkylamino preferably having 1 to 4, in particular 1 or 2, carbon atoms per alkyl group, such as methylamino, methyl-ethyl-amino, n- and i-propylamino and methyl-n-butylamino; carboxyl; carbalkoxy preferably having 2 to 4, in particular 2 or 3, carbon atoms, such as carbomethoxy and carboethoxy; sulpho (—SO$_3$H); alkylsulphonyl preferably having 1 to 4, in particular 1 or 2, carbon atoms, such as methylsulphonyl and ethylsulphonyl; arylsulphonyl preferably having 6 or 10 aryl carbon atoms, such as phenylsulphonyl, and also heteroarylamino and heteroarylalkylamino, such as chloropyridylamino and chloropyridylmethylamino.

A particularly preferably represents hydrogen and also represents optionally substituted radicals from the group consisting of acyl, alkyl, aryl, which are preferably defined as for R. A furthermore represents a bifunctional group. Mention may be made of optionally substituted alkylene having 1–4, in particular 1–2, carbon atoms, where the substituents which may be mentioned are the substituents listed further above and where the alkylene groups may be interrupted by heteroatoms from the group consisting of N, O and S.

A and Z together with the atoms to which they are attached may form a saturated or unsaturated heterocyclic ring. The heterocyclic ring may contain a further 1 or 2 identical or different heteroatoms and/or hetero groups. Preferred heteroatoms are oxygen, sulphur or nitrogen and preferred hetero groups are N-alkyl, where the alkyl of the N-alkyl group preferably contains 1 to 4, in particular 1 or 2, carbon atoms. Alkyls which may be mentioned are methyl, ethyl, n- and i-propyl and n-, i- and t-butyl. The heterocyclic ring contains 5 to 7, preferably 5 or 6, ring members.

Examples of the heterocyclic ring which may be mentioned are: pyrrolidine, piperidine, piperazine, hexamethyleneimine, hexahydro-1,3,5-triazine, morpholine, oxadiazine, each of which may optionally be substituted, preferably by methyl.

E represents an electron-withdrawing radical, and mention may be made in particular of NO$_2$, CN, halogenoalkylcarbonyl such as 1–5-halogeno-C$_{1-4}$-carbonyl, in particular COCF$_3$, and also alkylsulphonyl and halogenoalkylsulphonyl, such as 1–5-halogeno-C$_1$–C$_4$-sulphonyl, in particular SO$_2$CF$_3$.

X represents —CH═ or —N═.

Z represents optionally substituted radicals alkyl, —OR, —SR, —NRR (the radicals R are identical or different), where R and the substituents are preferably as defined above.

Z may, in addition to the abovementioned ring, form a saturated or unsaturated heterocyclic ring together with the atom to which it is attached and the radical

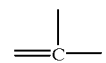

instead of X. The heterocyclic ring may contain a further 1 or 2 identical or different heteroatoms and/or hetero groups. Preferred heteroatoms are oxygen, sulphur or nitrogen and preferred hetero groups are N-alkyl, where the alkyl or N-alkyl group preferably contains 1 to 4, in particular 1 or 2, carbon atoms. Alkyls which may be mentioned are methyl, ethyl, n- and i-propyl and n-, i- and t-butyl. The heterocyclic ring contains 5 to 7, preferably 5 or 6, ring members.

Examples of the heterocyclic ring which may be mentioned are pyrrolidine, piperidine, piperazine, hexamethyleneimine, morpholine and N-methylpiperazine.

Particular mention may additionally be made of the use of compounds of the formula (I) which are characterized in that the radicals in the formula (I) are as defined below:

R represents optionally substituted radicals from the group consisting of heteroarylmethyl and heteroarylethyl, where heteroaryls which may be mentioned are:
thienyl, furyl, thiazolyl, imidazolyl, pyridyl, benzothiazolyl.

Substituents which may be mentioned are:
methyl, ethyl, methoxy, ethoxy, methylthio, ethylthio, trifluoromethyl; hydroxyl; fluorine, chlorine and bromine; cyano; nitro; amino;

A represents hydrogen and also represents a bifunctional, optionally substituted alkylene group having 2 carbon atoms which is attached to the radical Z, where the substituents which may be mentioned are the substituents listed further above and where the alkylene group may be interrupted by 1 heteroatom from the group consisting of N, O and S, A and Z together with the atoms to which they are attached may form a saturated or unsaturated 5- or 6-membered heterocyclic ring. The heterocyclic ring may contain a further 1 or 2 identical or different heteroatoms and/or hetero groups. Suitable heteroatoms are oxygen, sulphur or nitrogen and suitable hetero groups are N-alkyl, where the alkyl of the N-alkyl group contains 1 or 2 carbon atoms.

E represents NO$_2$, CN.

X represents —CH═ or —N═.

Z represents optionally substituted radicals alkyl, —OR', —SR', —NR'R' (the radicals R' are identical or different), where R' and the substituents are as defined below:

R' represents hydrogen and also represents optionally substituted radicals from the group consisting of acyl, alkyl, aryl, aralkyl, heteroaryl, heteroarylalkyl.

Acyl radicals which may be mentioned are formyl, alkylcarbonyl, arylcarbonyl, alkylsulphonyl, arylsulphonyl, (alkyl-)-(aryl-)-phosphoryl.

Alkyl which may be mentioned is C$_{1-4}$-alkyl.

Aryl which may be mentioned is phenyl.

Aralkyls which may be mentioned are phenylmethyl, phenylethyl.

Heteroarylalkyls which may be mentioned are heteroarylmethyl, heteroarylethyl, where the heteroaryls which may be mentioned are thienyl, furyl, thiazolyl. imidazolyl, pyridyl, benzothiazolyl.

Substituents of the radicals R' which may be mentioned are:

methyl, ethyl, methoxy, ethoxy, methylthio, ethylthio, halogenoalkyl having 1 or 2 carbon atoms and 1 to 5 halogen atoms, where the halogen atoms are identical or different and are fluorine, chlorine or bromine, hydroxyl; fluorine, chlorine and bromine; cyano, nitro, amino, monoalkyl- and dialkylamino preferably having 1 or 2 carbon atoms per alkyl group, carboxyl; carbalkoxy having 2 or 3 carbon atoms, sulpho (—SO$_3$H); alkylsulphonyl having 1 or 2 carbon atoms, phenylsulphonyl, chloropyridylamino and chloropyridylmethylamino.

Very particularly preferred compounds which can be used according to the invention which may be mentioned are the compounds of the general formulae (II), (III) and (IV):

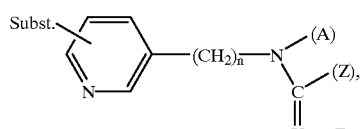

(II)

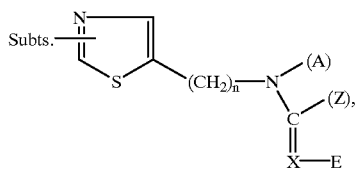

(III)

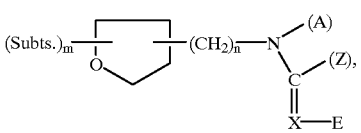

(IV)

in which n represents 1 or 2, m represents 0, 1 or 2,

Subst. represents one of the abovementioned substituents, in particular halogen, very particularly chlorine, A, Z, X and E are each as defined above.

Specifically, the following compounds may be mentioned:

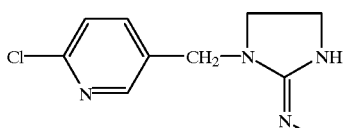

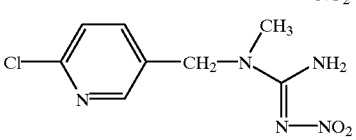

imidacloprid

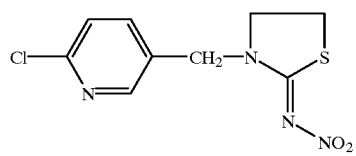

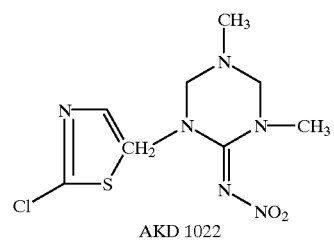

AKD 1022

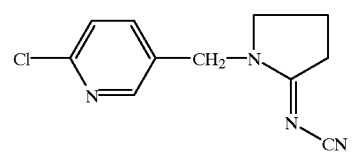

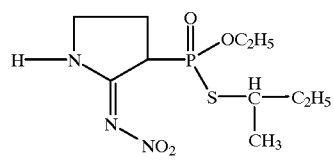

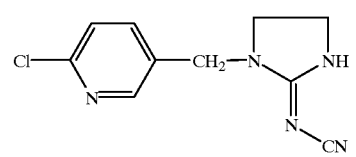

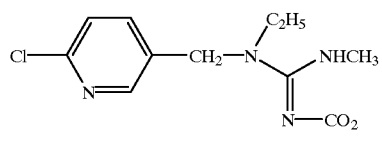

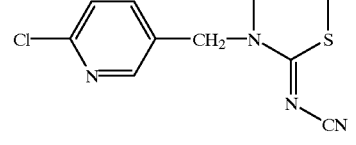

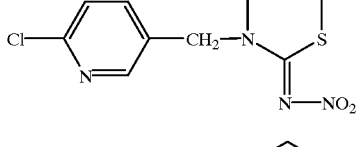

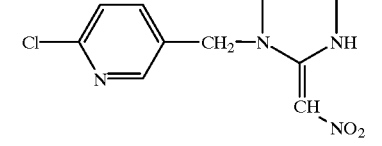

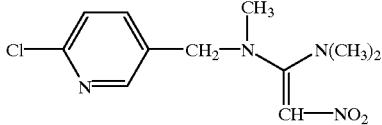

-continued
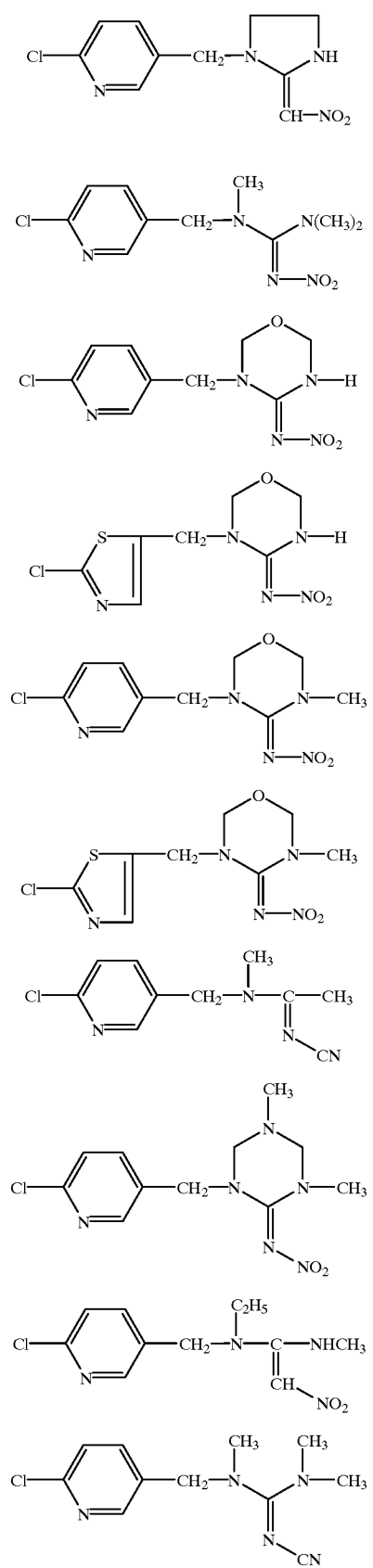
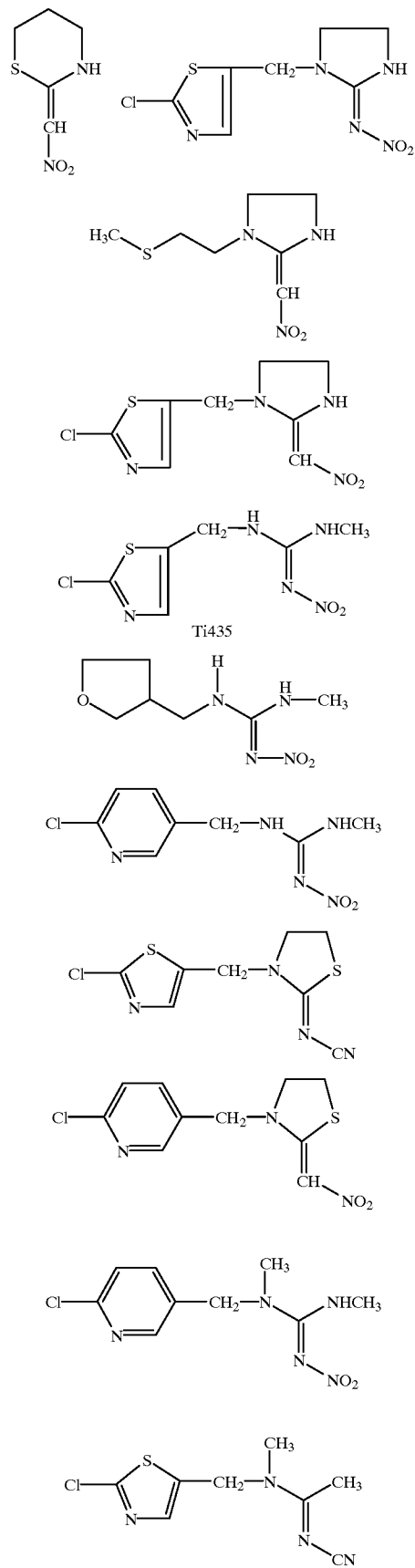

-continued

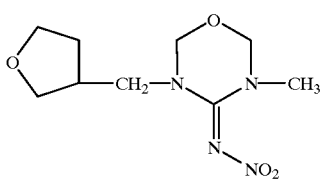

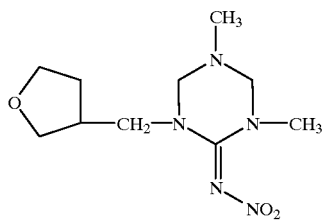

Particular emphasis is given to the compounds

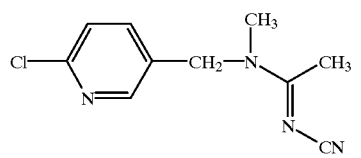

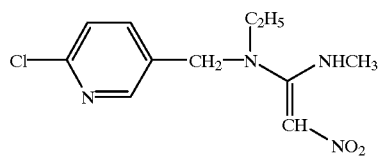

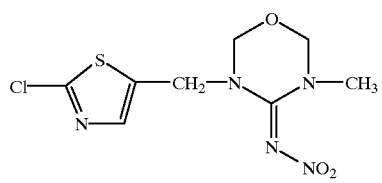

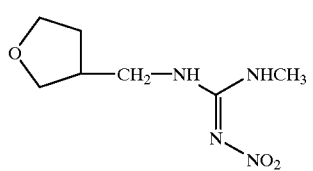

Furthermore, particular emphasis is given to the compounds

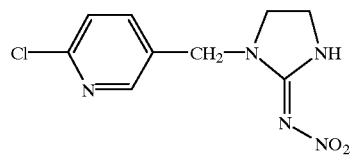

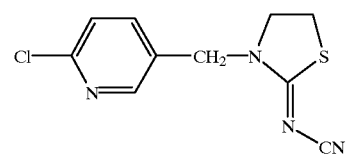

-continued

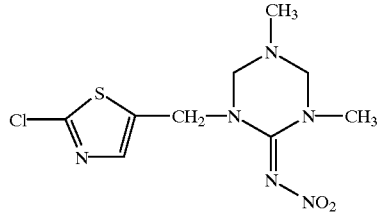

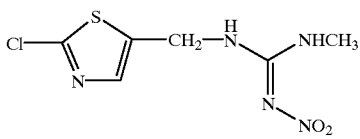

The active compounds are present in concentrations of from 0.0001 to 10% by weight, preferably from 0.1 to 10% by weight, particularly preferably from 0.2 to 2% by weight.

Water is present in concentrations of from 20 to 50% by weight, preferably from 25 to 45% by weight.

Acyclic alcohols which may be mentioned are aliphatic $C_{1-4}$-alkanols or diols, such as ethanol, isopropanol, diethylene glycol, furthermore 2-octyl-1-dodecanol and tetrahydrofurfuryl alcohol. Particular mention may be made of isopropanol. The alcohols are present in concentrations of from 20 to 50% by weight, preferably from 25 to 45% by weight. Preference is given to using a 60:40 to 50:50 alcohol/water-mixture.

Cyclic carbonates which may be mentioned are ethylene carbonate, propylene carbonate. Particular mention may be made of propylene carbonate. They are present in concentrations of from 2.5 to 30% by weight, preferably from 2.5 to 20% by weight, particularly preferably from 5 to 12.5% by weight.

Further suitable auxiliaries are: preservatives, such as benzyl alcohol, and perfumes and fragrances.

They are present in a concentration of from 0 to 15% by weight, preferably from 2.5 to 12.5% by weight, particularly preferably from 2.5 to 10.0% by weight.

The sum of active compounds, solvents and auxiliaries must be 100% by weight. Further auxiliaries are:

thickeners, for example inorganic thickeners, such as bentonites, colloidal silicic acid, aluminium monostearate, organic thickeners, such as cellulose derivatives, polyvinyl alcohols, polyvinylpyrrolidones and copolymers thereof, acrylates and methacrylates.

Colorants which may be mentioned are all colorants where use for the preparation of pharmaceuticals is permitted, which may be dissolved or suspended.

Auxiliaries which may be mentioned are spreading oils such as di-2-ethylhexyl adipate, isopropyl myristate, dipropylene glycol pelargonate, cyclic and acyclic silicone oils such as dimeticones, and their derivatives with cationic and anionic functional groups. A detailed description of silicones having cationic groups can be found, for example, in S. Marchioretto, J. Bakely, SOFW-Journal, 123, p. 881 (1997); B. Ziolkowsky, SOFW-Journal, 123, p. 822 (1997) and German Patent Specification 44 43 062. Their co- and terpolymers with ethylene oxide, propylene oxide and formalin, fatty acid esters, triglycerides and fatty alcohols are also suitable.

Antioxidants are, for example, sulphites or metabisulphites, such as potassium metabisulphite, ascorbic acid, butylated hydroxytoluene, butylated hydroxyanisole, tocopherol.

Light stabilizers are, for example, substances from the class of the benzophenones or novantisol acid.

Tackifiers are, for example, polymeric thickeners, for example cellulose derivatives, starch derivatives, polyacrylates, naturally occurring polymers such as alginates, gelatine.

Auxiliaries are also emulsifiers such as nonionic surfactants, for example polyethoxylated castor oil, polyethoxylated sorbitan-monooleate, sorbitan monostearate, glycerol monostearate, polyoxyethyl stearate, alkylphenol polyglycol ethers;

ampholytic surfactants, such as di-Na N-lauryl-B-iminodipropionate or lecithin;

anionic surfactants, such as Na-lauryl sulphate, fatty alcohol ether sulphates, mono/dialkylpolyglycol ether orthophosphoric ester-monoethanolamine salt;

cationic surfactants, such as cetyltrimethylammonium chloride.

Further auxiliaries are agents with which the formulations according to the invention can be sprayed or squirted or rubbed onto the skin. These are the conventional propellant gases required for spray cans, such as propane, butane, dimethyl ether, $CO_2$ or halogenated lower alkanes, or mixtures thereof with one another.

The amount of the abovementioned auxiliaries can be varied in the range of from 0 to 10% by weight, but preferably from 0.025 to 2.5% by weight.

While being of low toxicity to warm-blooded species, the formulations according to the invention are suitable for controlling parasitic insects which are encountered on humans. In this context they are active against all or individual stages of development of the pests and against resistant and normally sensitive species of the pests.

The pests include:

From the order of the Anoplura, for example, Pediculus spp., Pthirus spp.;

From the order of the Siphonaptera, for example, Ctenocephalides spp., Echidnophaga spp., Ceratophyllus spp.

Particular mention may be made of the activity against Anoplura and Siphonaptera. In this context, mention may be made of the activity against Pediculus humanus capitis (head lice), Pediculus humanus corporis (body lice) and Phthirus pubis (crab lice).

The formulations according to the invention may additionally contain juvenile hormones or juvenile-hormone-like substances, such as, for example, diaryl ethers, benzoylureas or triazines. These include, in particular, compounds of the following formulae:

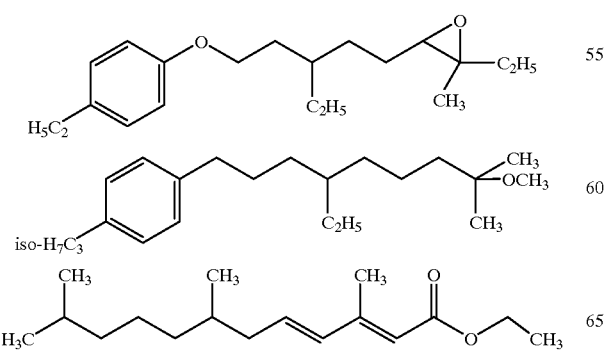

The substituted diaryl ethers include, in particular,

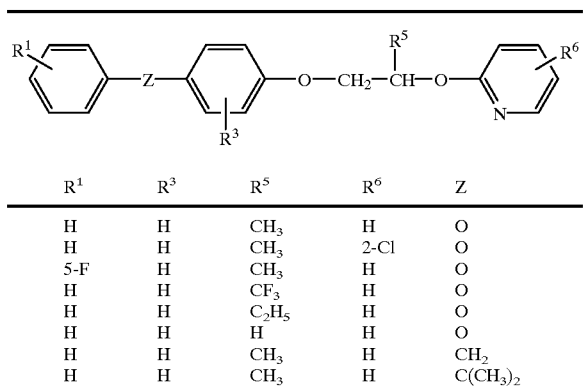

| $R^1$ | $R^3$ | $R^5$ | $R^6$ | Z |
|---|---|---|---|---|
| H | H | $CH_3$ | H | O |
| H | H | $CH_3$ | 2-Cl | O |
| 5-F | H | $CH_3$ | H | O |
| H | H | $CF_3$ | H | O |
| H | H | $C_2H_5$ | H | O |
| H | H | H | H | O |
| H | H | $CH_3$ | H | $CH_2$ |
| H | H | $CH_3$ | H | $C(CH_3)_2$ |

The benzoylureas include compounds of the formula

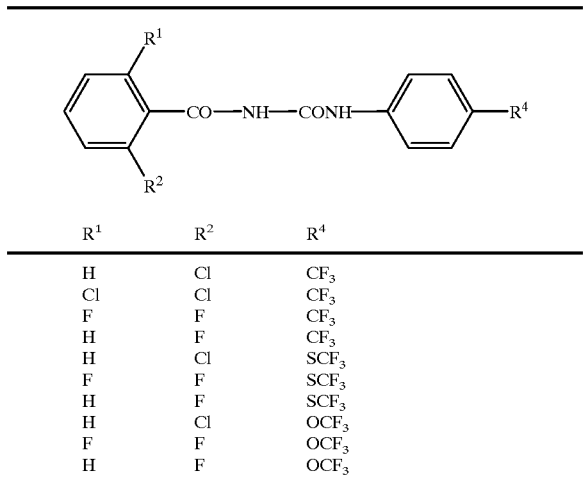

| $R^1$ | $R^2$ | $R^4$ |
|---|---|---|
| H | Cl | $CF_3$ |
| Cl | Cl | $CF_3$ |
| F | F | $CF_3$ |
| H | F | $CF_3$ |
| H | Cl | $SCF_3$ |
| F | F | $SCF_3$ |
| H | F | $SCF_3$ |
| H | Cl | $OCF_3$ |
| F | F | $OCF_3$ |
| H | F | $OCF_3$ |
| F | F | 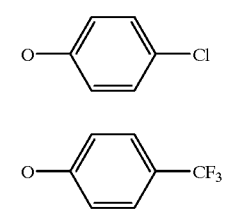 |
| F | F | |

-continued

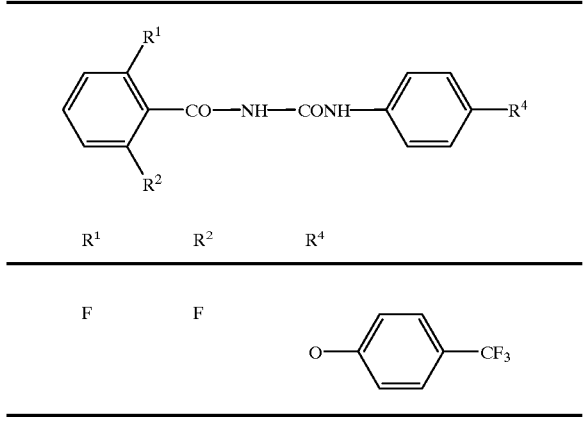

| R$^1$ | R$^2$ | R$^4$ |
|---|---|---|
| F | F | (structure shown) |

The triazines include compounds of the formula

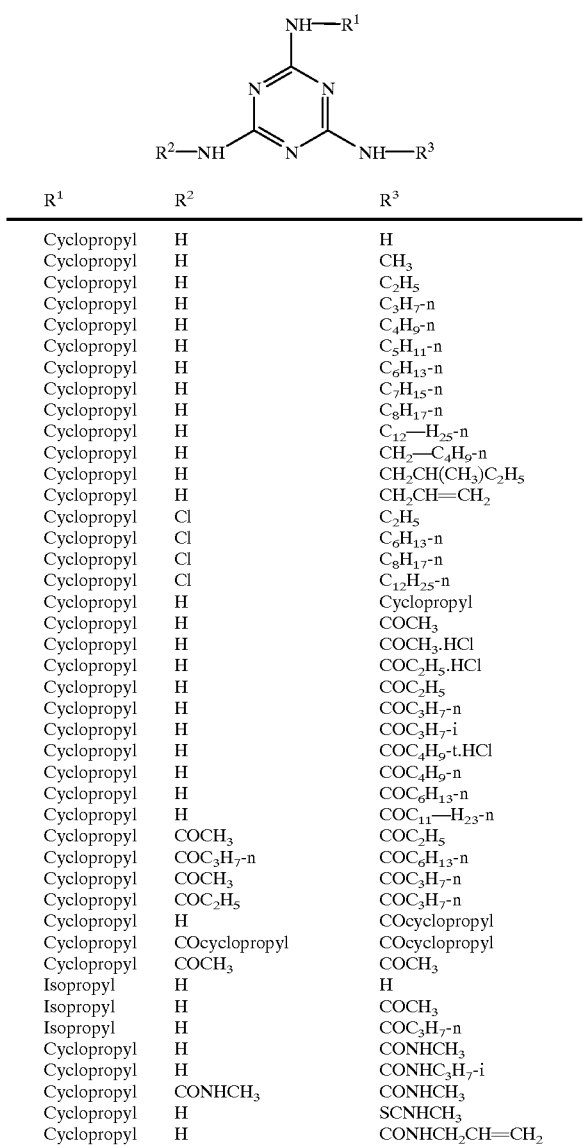

| R$^1$ | R$^2$ | R$^3$ |
|---|---|---|
| Cyclopropyl | H | H |
| Cyclopropyl | H | CH$_3$ |
| Cyclopropyl | H | C$_2$H$_5$ |
| Cyclopropyl | H | C$_3$H$_7$-n |
| Cyclopropyl | H | C$_4$H$_9$-n |
| Cyclopropyl | H | C$_5$H$_{11}$-n |
| Cyclopropyl | H | C$_6$H$_{13}$-n |
| Cyclopropyl | H | C$_7$H$_{15}$-n |
| Cyclopropyl | H | C$_8$H$_{17}$-n |
| Cyclopropyl | H | C$_{12}$—H$_{25}$-n |
| Cyclopropyl | H | CH$_2$—C$_4$H$_9$-n |
| Cyclopropyl | H | CH$_2$CH(CH$_3$)C$_2$H$_5$ |
| Cyclopropyl | H | CH$_2$CH=CH$_2$ |
| Cyclopropyl | Cl | C$_2$H$_5$ |
| Cyclopropyl | Cl | C$_6$H$_{13}$-n |
| Cyclopropyl | Cl | C$_8$H$_{17}$-n |
| Cyclopropyl | Cl | C$_{12}$H$_{25}$-n |
| Cyclopropyl | H | Cyclopropyl |
| Cyclopropyl | H | COCH$_3$ |
| Cyclopropyl | H | COCH$_3$.HCl |
| Cyclopropyl | H | COC$_2$H$_5$.HCl |
| Cyclopropyl | H | COC$_2$H$_5$ |
| Cyclopropyl | H | COC$_3$H$_7$-n |
| Cyclopropyl | H | COC$_3$H$_7$-i |
| Cyclopropyl | H | COC$_4$H$_9$-t.HCl |
| Cyclopropyl | H | COC$_4$H$_9$-n |
| Cyclopropyl | H | COC$_6$H$_{13}$-n |
| Cyclopropyl | H | COC$_{11}$—H$_{23}$-n |
| Cyclopropyl | COCH$_3$ | COC$_2$H$_5$ |
| Cyclopropyl | COC$_3$H$_7$-n | COC$_6$H$_{13}$-n |
| Cyclopropyl | COCH$_3$ | COC$_3$H$_7$-n |
| Cyclopropyl | COC$_2$H$_5$ | COC$_3$H$_7$-n |
| Cyclopropyl | H | COcyclopropyl |
| Cyclopropyl | COcyclopropyl | COcyclopropyl |
| Cyclopropyl | COCH$_3$ | COCH$_3$ |
| Isopropyl | H | H |
| Isopropyl | H | COCH$_3$ |
| Isopropyl | H | COC$_3$H$_7$-n |
| Cyclopropyl | H | CONHCH$_3$ |
| Cyclopropyl | H | CONHC$_3$H$_7$-i |
| Cyclopropyl | CONHCH$_3$ | CONHCH$_3$ |
| Cyclopropyl | H | SCNHCH$_3$ |
| Cyclopropyl | H | CONHCH$_2$CH=CH$_2$ |

-continued

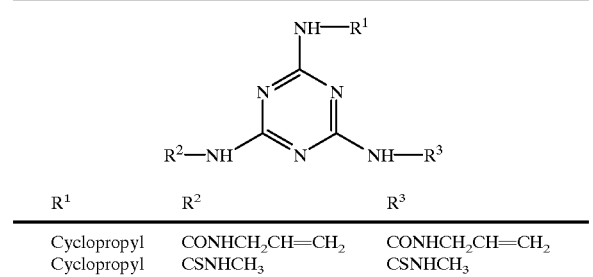

| R$^1$ | R$^2$ | R$^3$ |
|---|---|---|
| Cyclopropyl | CONHCH$_2$CH=CH$_2$ | CONHCH$_2$CH=CH$_2$ |
| Cyclopropyl | CSNHCH$_3$ | CSNHCH$_3$ |

The amount of the additional active compounds may be from 0 to 10% by weight, based on the overall mass of the formulation, preferably up to 7.5%, particularly preferably up to 5.0%.

Active compounds which can be used according to the invention that may be mentioned are imidacloprid, AKD 1022 and Ti 435.

AKD 1022 is a chloronicotinyl derivative of the formula

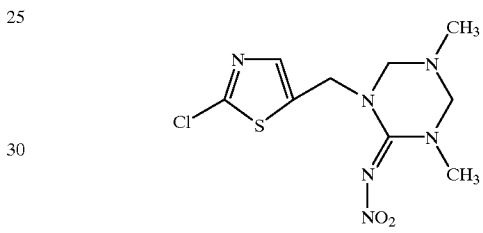

Ti 435 is a chloronicotinyl derivative of the formula

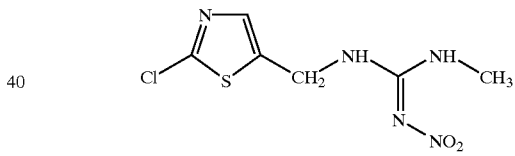

It is surprising that, by using water, if appropriate in combination with spreading agents and auxiliaries, the parasitizidic activity is improved considerably. This leads to a reduction in the dosage of the active compounds.

In the examples below, the active compound used is 1-[(6-chloro-3-pyridinyl)methyl]-4,5-dihydro-N-nitro-1H-imidazole-2-amine (common name imidacloprid).

EXAMPLE 1

Imidacloprid Lotion 1.0% w/v

| | | |
|---|---|---|
| Imidacloprid | 1.000 g | a.i. |
| Isopropyl alcohol/water (60:40) | 79.796 g | solvent |
| Propylene carbonate | 10.000 g | solvent |
| | 90.796 g = 100.0 ml | |

EXAMPLE 2

Imidacloprid Lotion 1.0% w/v

| | | |
|---|---|---|
| Imidacloprid | 1.000 g | a.i. |
| Isopropyl alcohol/water (60:40) | 79.026 g | solvent |
| Propylene carbonate | 10.000 g | solvent |
| ®Cetiol HE*⁾ | 1.000 g | surfactant |
| | 91.026 g = | 100.0 ml |

*⁾(A polyethylene glycol monococonant from Henkel AG)

EXAMPLE 3

Imidacloprid Lotion 1.0% w/v

| | | |
|---|---|---|
| Imidacloprid | 1.000 g | a.i. |
| Isopropyl alcohol/water (60:40) | 79.026 g | solvent |
| Propylene carbonate | 10.000 g | solvent |
| ®Abil Quart 3272**⁾ | 1.000 g | surfactant, hair conditioner |
| | 91.026 g = | 100.0 ml |

**⁾(Polysiloxane copolymer having quaternary ammonium groups from Goldschmidt AG).

EXAMPLE 4

Imidacloprid Lotion 1.0% w/v

| | | |
|---|---|---|
| Imidacloprid | 1.000 g | a.i. |
| Isopropyl alcohol/water (60:40) | 84.044 g | solvent |
| Propylene carbonate | 10.000 g | solvent |
| | 95.044 g = | 100.0 ml |

EXAMPLE 5

Imidacloprid Lotion 1.0% w/v

| | | |
|---|---|---|
| Imidacloprid | 1.000 g | a.i. |
| Isopropyl alcohol/water (60:40) | 83.402 g | solvent |
| Propylene carbonate | 10.000 g | solvent |
| ®Cetiol HE*⁾ | 1.000 g | surfactant |
| | 95.402 g = | 100.0 ml |

*⁾(A polyethylene glycol monococonant from Henkel AG)

EXAMPLE 6

Imidacloprid Lotion 1.0% w/v

| | | |
|---|---|---|
| Imidacloprid | 1.000 g | a.i. |
| Isopropyl alcohol/water (60:40) | 83.402 g | solvent |

-continued

| | | |
|---|---|---|
| Propylene carbonate | 10.000 g | solvent |
| ®Abil Quart 3272**⁾ | 1.000 g | surfactant, hair conditioner |
| | 95.402 g = | 100.0 ml |

**⁾(Polysiloxane copolymer having quaternary ammonium groups from Goldschmidt AG).

Use Example A
Pediculus/Wild Population

The lice used were from a wild population (Pediculus humanus capitis) which were obtained from the carriers by combing and which were used for the experiments directly after having been obtained. The lice eggs (nits) used were likewise taken freshly from the hair of infested volunteers and prepared for the test (one nit per cut hair).

Application was carried out by a reality-like imitation of using a lotion by dip treatment of lice and nits. In test groups of 15 specimens, adult lice were exposed to the test solutions for 5 to 10 min. The nits with the associated carrier hair were dipped into the test solutions in test groups of 10 specimens, in each case for 10 min. After the respective incubation phase had expired, lice and nits were washed with water and dried. The effectiveness of the treatment was determined to be 100% in the case of adult lice after 3 h and to be 100% in the case of nits after 12 d (inhibition of hatching).

Use Example B
Pediculus/Laboratory Strain

The lice used were from a laboratory population (Pediculus humanus humanus) and were taken freshly from the cultivation cycle. The louse eggs (nits) used were likewise obtained freshly after oviposition by adult females onto fibre web plates and prepared for the examination.

Application was carried out by a reality-like imitation of using a lotion by dip treatment of lice and nits. In test groups of 20 specimens, adult lice were exposed to the test solutions for 10 sec. The nits with the associated carrier hair were dipped into the test solutions in test groups of 20 specimens, in each case for 10 min. After the respective incubation phase had expired, lice and nits were washed with water and dried. The effectiveness of the treatment was determined to be 100% in the case of adult lice after 24 h and to be 100% in the case of nits after 12 d (inhibition of hatching).

What is claimed is:

1. A formulation for dermal application for the control of parasitic insects and mites on humans comprising:
   (a) from 0.0001% to 7.5% by weight, based on the total weight of the formulation, of at least one active compound selected from the group consisting of agonists and antagonists of the nicotinic acetylcholine receptors of insects;
   (b) from 20% to 50% by weight water, based on the total weight of the formulation;
   (c) from 20% to 50% by weight, based on the total weight of the formulation, of at least one acyclic alcohol;
   (d) from 2.5% to 30% by weight, based on the total weight of the formulation, of at least one cyclic carbonate; and
   (e) from 0% to 30% by weight, based on the total weight of the formulation, of at least one auxiliary ingredient selected from the group consisting of: thickeners, spreading agents, colorants, antioxidants, propellants, preservatives, tackifiers, and emulsifiers.

2. The formulation of claim 1, wherein said active compound is selected from the group consisting of:

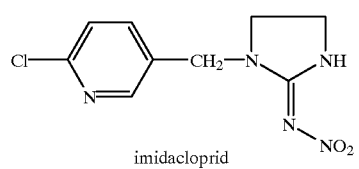
imidacloprid
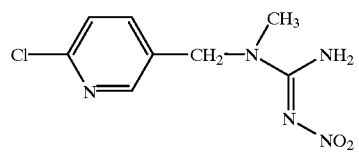
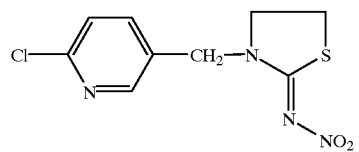
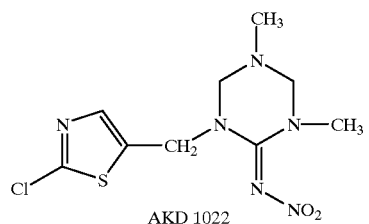
AKD 1022
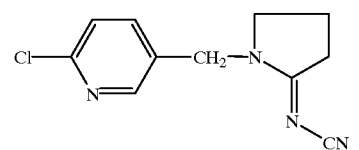
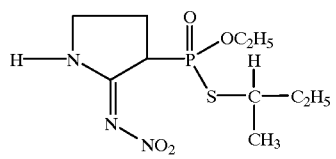
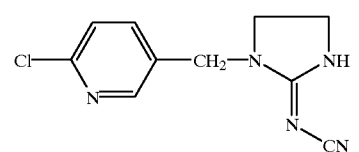
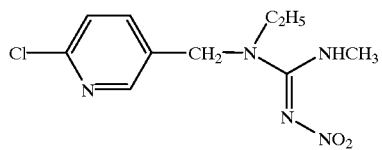
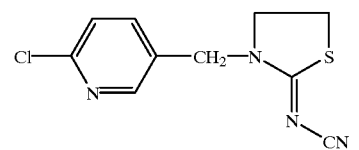
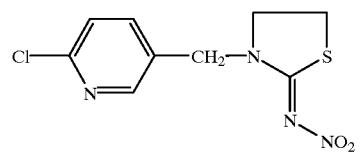
-continued
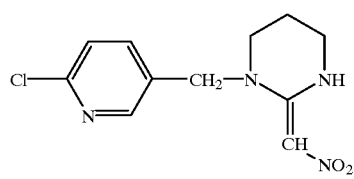
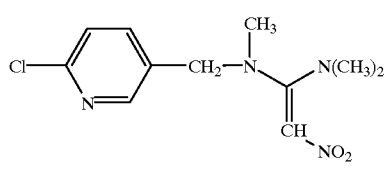
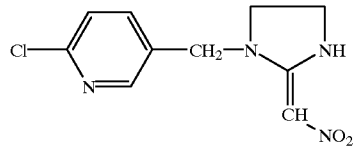
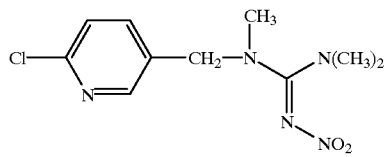
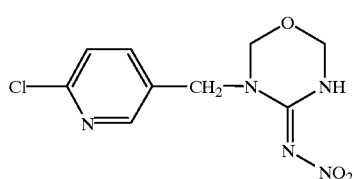
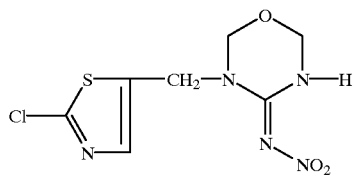
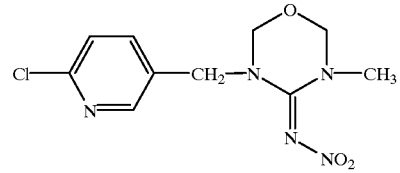
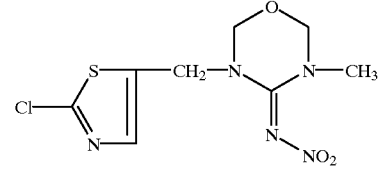
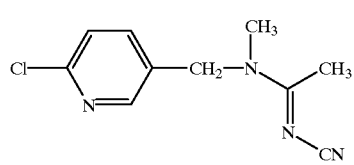

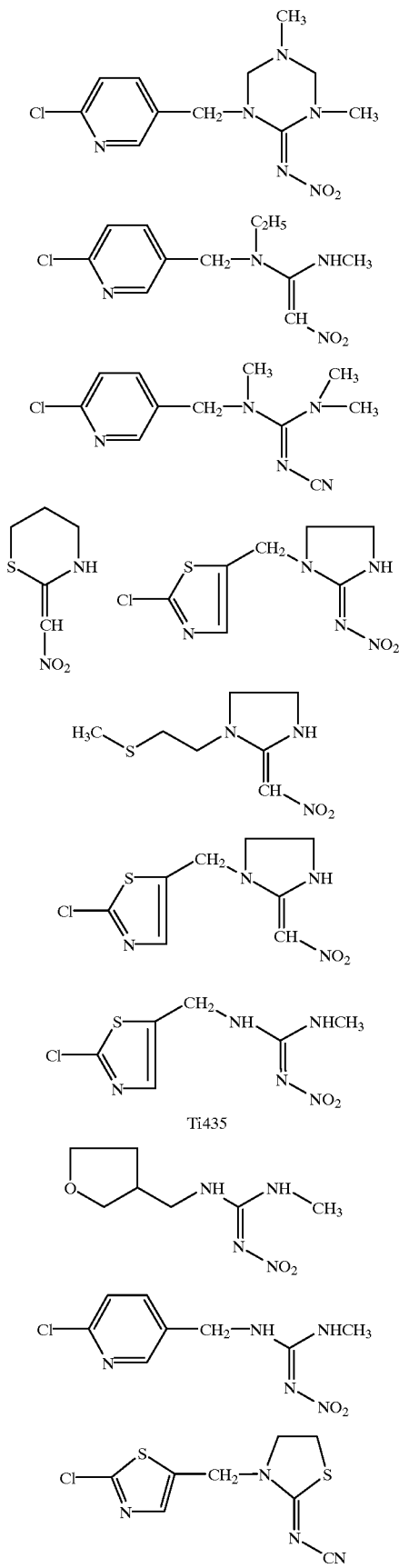

Ti435

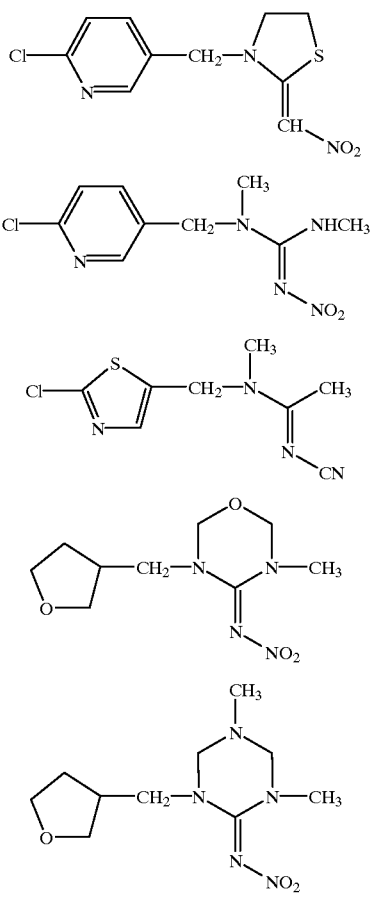

3. The formulation of claim 1, herein said active compound is at least one compound having the formula (I):

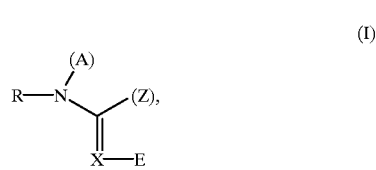

(I)

wherein R represents (a) hydrogen or (b) optionally substituted radicals selected from the group consisting of acyl, alkyl, aryl, aralkyl, heteroaryl, heteroarylalkyl, and heterocyclalkyl radicals;

wherein A represents (a) a monofunctional group selected from the group consisting of hydrogen, acyl, alkyl, and aryl and (b) a bifunctional group;

wherein E represents an electron-withdrawing radical;

wherein X represents the radicals —CH═, or ═N—; and wherein Z represents (a) a monofunctional group selected from the group consisting of alkyl, —O—R, —S—R, and —N—$R_1R_2$, wherein $R_1$ and $R_2$ are as defined above for R and may be the same or different, or (b) a bifunctional group.

4. The formulation of claim 3, wherein said active compound is at least one compound having the formula (I):

(I)

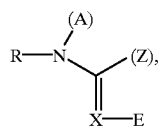

wherein R represents (a) hydrogen or (b) optionally substituted radicals selected from the group consisting of (i) thienyl, (ii) furyl, (iii) thiazolyl, (iv) imidazolyl, (v) pyridyl, and (vi) benzothiazolyl groups, wherein said radicals may be substituted with at least one group selected from the group consisting of methyl, ethyl, methoxy, ethoxy, methylthio, ethylthio, trifluoromethyl, hydroxyl, flouro, chloro, bromo, cyano, nitro, and amino groups, wherein A represents (a) hydrogen or (b) a bifunctional, optionally substituted, alkylene group having two carbon atoms, wherein said alklyene group is also attached to substituent Z, further wherein said alkylene group may further comprise one heteroatom from the group consisting of nitrogen, oxygen and sulfur, between said two carbon atoms, wherein substituent A and substituent Z, together with the atoms to which they are attached, may optionally form a saturated or unsaturated five or six member heterocyclic ring, wherein said heterocyclic ring may contain at least one heteroatoms or heterogroup selected from the group consisting of oxygen, sulfur, nitrogen and N-alkyl groups, wherein the alkyl of said N-alkyl group contains from one to two carbon atoms, wherein E represents $NO_2$, or CN, wherein X represents —CH= or —N=, and wherein Z represents (a) optionally substituted radicals selected from the group consisting of alkyl, —OR, —SR, and —$NR_1R_2$, wherein $R_1$ and $R_2$ may be the same or different, and wherein R, $R_1$ and $R_2$ are selected from the group consisting of hydrogen, and optionally substituted radicals selected from the group consisting of acyl, alkyl, aryl, aralkyl, heteroaryl, heteroarylalkyl groups.

5. The formulation of claim 3, wherein said active compound is at least one compound selected from the formulae (II, III, and IV):

(II)

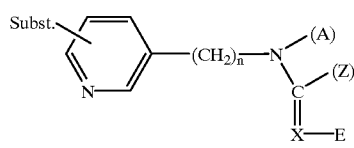

(III)

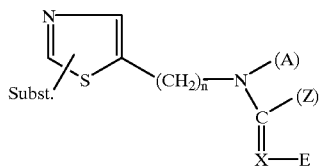

(IV)

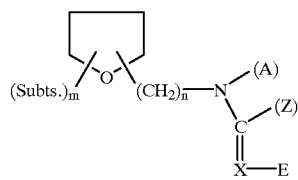

wherein n represents 1 or 2, wherein m represents 0, 1, or 2;

wherein subst. represents a substituent;

wherein A represents (a) hydrogen or (b) a bifunctional optionally substituted alkylene group having two carbon atoms that is attached to the radical Z, wherein said alkylene group may be interrupted by one heteroatom selected from the group consisting of nitrogen, oxygen, and sulfur, wherein E represents $NO_2$ or CN, wherein X represents —CH= or —N=, and wherein Z represents optionally substituted radicals selected from the group consisting of alkyl, —OR, —SR, and —$NR_1R_2$, wherein $R_1$ and $R_2$ may be the same or different, and wherein R, $R_1$ and $R_2$ may be hydrogen or optionally substituted radicals selected from the group consisting of acyl, alkyl, aryl, aralkyl, heteroaryl and heteroarylalkyl groups.

6. The formulation of claim 1, wherein said acyclic alcohol is selected from the group consisting of: aliphatic $C_{1-4}$ alkanols and diols.

7. The formulation of claim 6, wherein said acyclic alcohol is selected from the group consisting of: ethanol, isopropanol, diethylene glycol, 2-octyl-1-dodecanol and tetrahydrofurfuryl alcohol.

8. The formulation of claim 1, wherein said acyclic alcohol comprises from 25% to 45% of said formulation by weight.

9. The formulation of claim 1, wherein the weight ratio of said acyclic alcohol to said water is from 60:40 to 50:50.

10. The formulation of claim 1, wherein said cyclic carbonate is selected from the group consisting of: ethylene carbonate and propylene carbonate.

11. The formulation of claim 1, wherein said cyclic carbonate comprises from 2.5% to 20% by weight of said formulation.

12. The formulation of claim 1, wherein said cyclic carbonate comprises from 5% to 12.5% by weight of said formulation.

13. The formulation of claim 1, wherein said auxiliary ingredient is selected from the group consisting of: preservatives, perfumes and fragrances and combinations thereof.

14. A process for controlling parasitic insects or mites comprising the step of applying a formulation comprising the formulation of claim 1 to the skin or clothes of a human.

* * * * *